United States Patent [19]
Yun

[11] Patent Number: 5,643,333
[45] Date of Patent: Jul. 1, 1997

[54] BIOLOGICAL ENERGY PROJECTOR

[76] Inventor: Young-Ung Yun, Room 716, The Korea Federation of Small Business Bldg. 16-2, Yoido-dong, Youngdeungpo-ku, Seoul, Rep. of Korea

[21] Appl. No.: 340,855

[22] Filed: Nov. 15, 1994

[51] Int. Cl.$^6$ ..................................................... A61N 5/00
[52] U.S. Cl. ..................... 607/88; 607/90; 362/293
[58] Field of Search ............................. 313/111; 362/255, 362/256, 293; 607/88, 90–94

[56] References Cited

U.S. PATENT DOCUMENTS

| | | | |
|---|---|---|---|
| 4,505,575 | 3/1985 | Sclia-Munoz | 607/90 |
| 5,083,252 | 1/1992 | McGuire | 362/393 |

FOREIGN PATENT DOCUMENTS

| | | | |
|---|---|---|---|
| 2105195 | 3/1983 | United Kingdom | 607/88 |

OTHER PUBLICATIONS

Article entitled "A Study on the Function of Biological Energy Projector for Immune Cells" by Prof. C.J. Kim, et al. of Institute of Veterinary Science, Choong Nam University, Korea.

Translation of a Decision Given on the Clinical Test of a Medical Appliance Article entitled "The Mechanical Properties of a Biological Energy Projector (BEP) and an Effect Produced by the BEP on Water" by Park Ho Goon, Korea Institute of Science & Technology dated Dec. 27, 1994.

Article entitled "The Biologic Electron Re-Examining the Work of Johanna Budwig" by Dan C. Roehm, Townsend Letter for Doctors Jul. 1990.

The Biotron, vol. 1, Issue 1, Jan. 1991.

Paper entitled "Study on the Carcinostatic Effect by Biological Energy Projector" read in the 11th annual meeting of the Korean Association for Laboratory Animal Science on May 26–27, 1995.

*Primary Examiner*—Robert L. Nasser
*Attorney, Agent, or Firm*—Michael D. Bednarek; Kilpatrick Stockton LLP

[57] ABSTRACT

The present invention relates to projection of biological energy on living things. The biological energy projector of the present invention comprises a photon producing means which produces an original photon from an outside power source, an energy changing means which changes the produced photon and an energy adjusting means which adjusts the changed energy to energy which is projected on a living thing but penetrates a lifeless thing.

14 Claims, 2 Drawing Sheets

BIOLOGICAL ENERGY PROJECTOR

BACKGROUND OF THE INVENTION

The present invention relates to projection of biological energy on living things. In particular, the invention relates to a biological energy projector in which a photon produced by an electric bulb is reinforced in piles by the interaction of photon energy separated into its spectral components by a multiprism and photoelectron energy released by a reflecting plate and energy useful to a living body is created through a color balancer and emanated to the outside.

In order for a living thing to maintain its life and lead on a healthy life, required energy must be supplied continuously.

A basic energy source is obtained by ingesting those materials produced by primary producers like green plants through food and drink and gradually reducing them into their components together with breathing after storing them in the body.

Photosynthetic action in green plants is a reaction of synthesizing organic matter from carbon dioxide by absorbing a photon. At this time, these plants conduct very important metabolism which maintains the environment of the earth and all living things by imbibing carbon dioxide in the atmosphere and discharging oxygen.

Such a photosynthetic action is achieved when the chlorophyll of a plant absorbs a photon.

The organic matter created by the plant is ingested by animals including men and used as a source of energy (ATP). In the cell of an animal, it is reduced into a source of energy (ATP), water and carbon dioxide through metabolism.

In the process of this metabolism, energy charged with an electric charge such as ion is produced and ATP serves as storing electron energy.

Thus, a living thing obtains energy indirectly by changing it variously.

According to literature, the energy directly obtained in the human body produces energy useful to a living body when indispensable fatty acid in the human body interact with electrons flowing therein by absorbing a photon. (Dr. J. Budwig).

The aforesaid indispensable fatty acids (linolenic and linoleic acids) have the following structural formulae.

Linoleic Acid LA 18:2w6

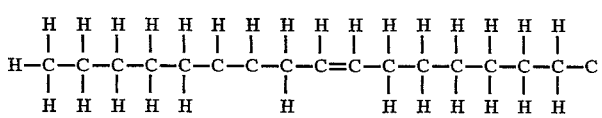

Linolenic Acid LNA 18:3w3

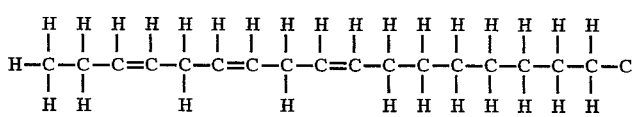

G. Lakhovsky, a physicist born in the Soviet Union, compared the shape of a cell nucleus to a general electric wire in his "The secrets of life".

The nutritious material such as indispensable fatty acid and amino acid in the cell serves as the inductance of an electric wire. According to him, it sets up a vibration and causes and an oscillation by the interaction of photon energy.

When the energy obtained through such an action keeps the oscillation faithfully in the cell, a living thing maintains its life, improves health, strengthens immunity and smoothens cell division, he stated.

It is revealed that photon energy is the root of such an action.

Accordingly, it is proved that photon energy coming from light functions as a decisive factor in life conservation in all living things.

SUMMARY OF THE INVENTION

Therefore, the present invention aims to provide a biological energy projector which easily projects required energy in order to activate a living thing by producing energy useful to the human body and projecting it directly thereon practically applying the principle of producing energy in the cell with a device.

The present invention intended to accomplish such an object comprises a photon energy producing means, an energy changing means, an energy adjusting means and a stainless steel tube which protects said each means and serves as a reflecting plate at the same time.

In other words, the present invention comprises a photon energy producing means equipped with a power switch, a plug and a socket so as to produce photon energy by the supply of a power source, an energy changing means provided with a multiprism and a stainless steel tube so as to change photon energy produced from the photon energy producing means by spectral diffraction, mutual interference and superposition, and an energy adjusting means made up of a color balancer, prism disks and an energy transmitting part so as to adjust the energy changed by the energy changing means.

When a power source is supplied by operating a switch installed at the rear end of the stainless steel tube, a fluorescent light bulb, which is a photon producing means, is lighted and an electric field is developed into electromagnetic wave by undergoing a sudden change and the photon appears even in the state of a particle which is a photon other than in the state of a wave motion.

Moreover, the photon is separated into its spectral components by the multiprism which is an energy changing means and electrons are produced by the photoelectric effect upon striking against a reflecting plate.

As another embodiment of the present invention, a grounding device is installed around the bulb 4, a photon producing means, as shown in FIG. 2.

The grounding device is formed by connecting a metal net 11 installed to cover the girth of the bulb 4 to a plug 1 with an ground wire 12.

Consequently, harmful electromagnetic waves produced from the bulb 4 are intercepted by the metal net 11 and grounded by the ground wire 12.

The electron energy is mixed with photon energy and transformed into energy useful to the human body by a reciprocal action.

For reasons of convenience, energy useful to the human body is named "bioenergy" or "biotron=bioelectron".

In the present device, energy separated into its spectral components by the multiprism and a photoelectron emanated by the reflecting plate, namely, electron energy co-exist and interact. The energy produced by this interaction is uniformly distributed by the blue color balancer, which is an energy adjusting means. After it is reinforced in piles through each prism disk, it is released to the outside.

The energy produced in this way is absorbed into the living body by indispensable fatty acids through sympathetic vibration of wave motions and gives various effects.

This energy has the same wavelength as that of a living thing, and so it is absorbed into the living thing, but a lifeless thing transmits it.

DETAILED DESCRIPTION OF THE EMBODIMENT

Figure 1:
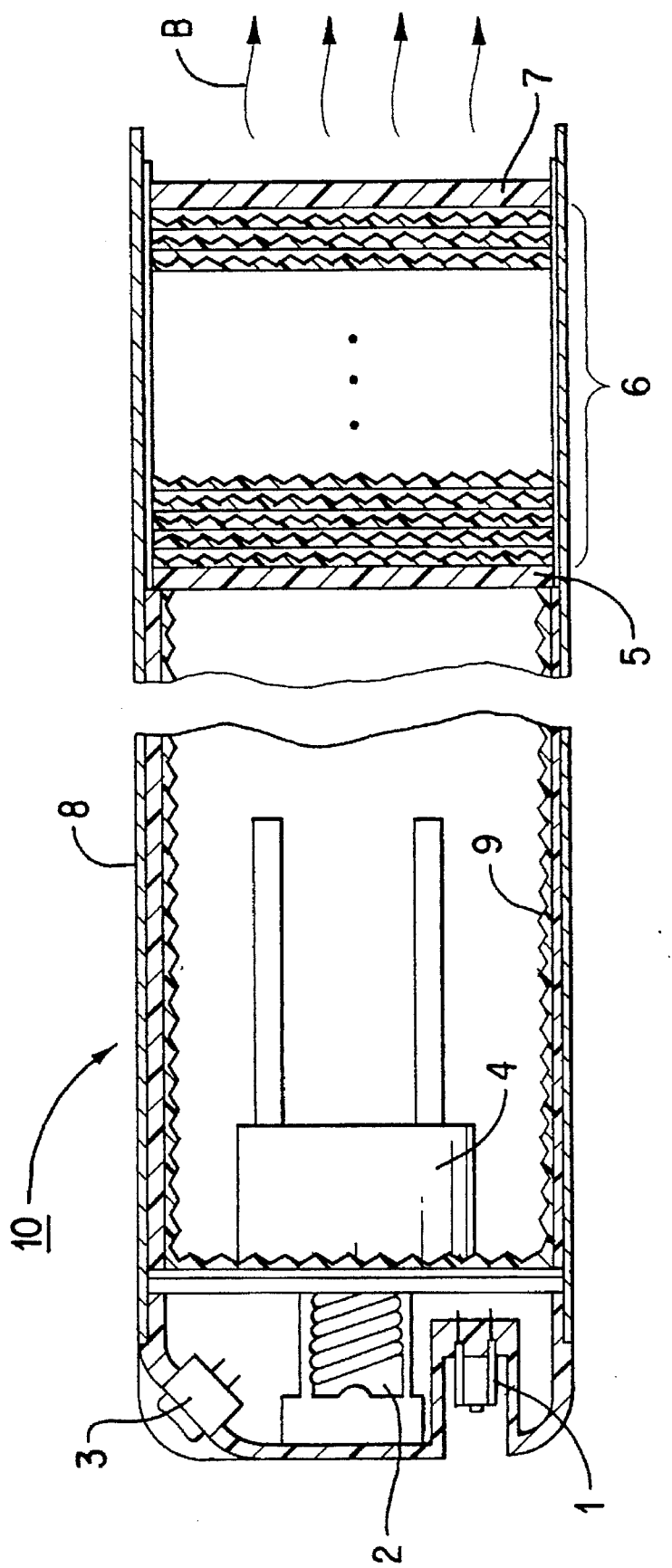
FIG. 1 is a lateral sectional view showing an embodiment of the present invention.
Figure 2:
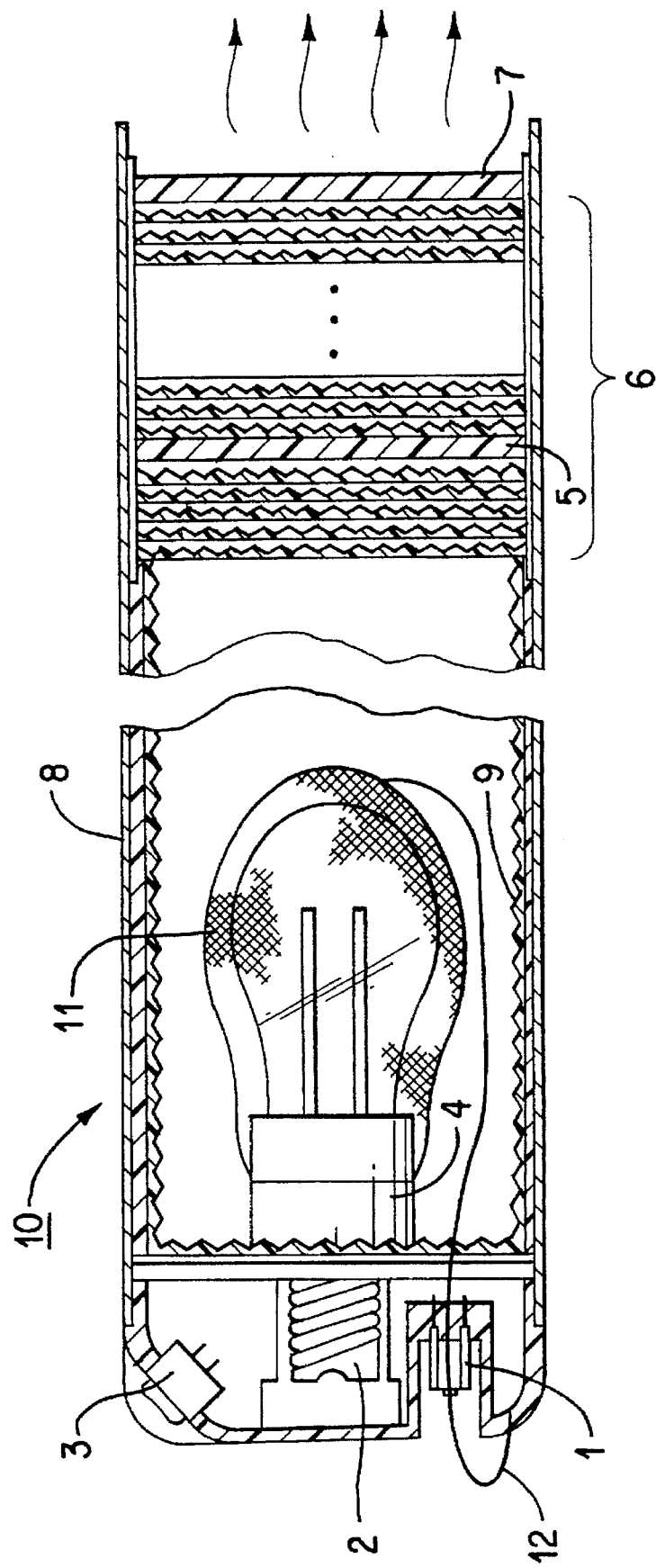
FIG. 2 is a lateral sectional view showing another embodiment of the present invention.

An embodiment of the present invention will now be described in detail.

The present invention comprises a photon producing means which produces an original photon from an outside power source, an energy changing means which changes the produced photon and an energy adjusting means which adjusts the changed energy to energy which is projected on a living thing but penetrates a lifeless thing.

The photon producing means is equipped with a usual bulb 4 which changes electric energy into a photon, a socket 2 and a power switch 3.

For the bulb 4, a fluorescent white light bulb or a general light bulb is used. The bulb 4 is inserted into the socket 2 installed in the inner central part. It is installed so as to release the photon from the inner central part of the multiprism 9.

The energy changing means comprises a multiprism 9 and a powerfully reflecting stainless steel tube 8 which covers the multiprism.

In other words, the energy changing means comprises a stainless steel tube 8 which produces electrons by the reflection and photoelectric effect and a multiprism 9 installed in the inner side of the stainless steel tube 8 to separate a photon into its spectral components and diffuse its reflection.

For the multiprism 9, an acrylic prism which is uneven on one side is used.

The concavo-convex part of this prism 9 is formed of height-uniformalized triangular projections.

The stainless steel tube 8 is cylindrical and functions as an outer case which protects all components of the present device and as a reflecting plate.

It suffers no inconvenience if other metallic material excellent in photoelectric effect and reflective power is used instead of the stainless steel tube 8.

The energy adjusting means comprises a blue acrylic color balancer 5 and a number of acrylic prism disks 6 installed in layers on the backside thereof.

Accordingly, it is possible for a photon to be refracted, to be separated into its spectral components, to be interfered mutually and to be piled one on each other.

The color balancer 5 is a plate-shaped filter with a thickness of 1 to 5 mm formed by mixing a blue pigment into genuine acryl. It adjusts energy uniformly to monochromatic light, i.e. blue frequency energy.

In the energy transmitting part in front, a black body acrylic plate 7 is installed.

Now, working and effect of the present invention will be described in detail.

When a power source is supplied to the energy producing means through the power switch 3, the bulb 4 inserted into the socket 2 emits a photon.

The photon produced by the photon producing means is partially separated into its spectral components and reflected diffusibly and some of light which passed through the multiprism 9 is reflected by running against the surface of the stainless steel tube 8.

The multiprism 9 is made of acrylic material having molecular structure of —C=C—C=O. Its molecular structure is common to linolenic and linoleic acids in the human body. It makes an interaction with photoelectrons possible by absorbing a photon, according to Dr. J. Budwig.

The photon is the one in which those lights which are various in wavelength are mixed and mutual interference is made by repeating multiple reflection and spectral diffraction.

At the same time, the photon produces photoelectrons by striking against the surface of the stainless steel tube 8.

Said each energy is mixed in the device and is changed by an interaction.

The energy changed in this way is uniformly adjusted while passing through the color balancer 5.

The color balancer 5 is blue-colored acrylic filter. It is known that the blue color effect in living things proved very efficacious for lymphocytes.

The energy uniformly adjusted by the color balancer 5 is reinforced in layers and adjusted by the continuous spectral diffraction and interference while passing through a layer-built prism disk 6.

As to the adjusted energy, only energy having sufficient intensity to penetrate black body acrylic plate 7, i.e. converted energy, is passed or transmitted to the outside through a black body acrylic plate 7 in front.

This energy that has passed through the black body acrylic plate is the same as biological energy in the number of vibrations generate a field in which energy cell of the human body could find its own frequency and vibrate in resonance and so its effect is ideal when it resonates. Lakhvosky called it "resonance absorption".

As a test of the present invention, the function, form and nature of an immunized cell was analyzed.

Before and after the test on 20 20-day old pigs and 20 white rats, peripheral blood was taken and distribution of leukocytes by subgroups was examined with monoclonal antibody.

Moreover, cell growth promotion effect was examined comparatively by means of $^3$H-thymidine absorption method.

<Examination of the Distribution of Immunized Cells in the Animal Body>

As the result of examining the distribution of leukocytes by subgroups using a monoclonal antibody after peripheral blood is taken before and after the test, CD4 and SIgM showed a little higher increase.

In particular, CD2 and CD8 showed a remarkable rise as a phenomenon of high revelation to 28.7% and 20.0% respectively after the test from 17.1% and 10.8% before the test.

<Examination of Cell Growth Promotion Effect>

After lymphocytes are separated from the peripheral blood of a pig before an dafter the test, mitogen stimulation was provided thereto by means of Con A and PWM, and CPM was measured. As a result, it showed a higher cell promotion effect in the lymphocytes of a group irradiated by the present invention than in a group not irradiated.

The test showed that a higher cell growth promotion effect was produced in the biological energy-irradiated group even in the case of white rats.

As described hereinabove, the present invention makes a photon into photoelectric energy in the process where electrons released due to spectral diffraction and diffused reflection of a simple photon by the multiprism and its reflection and photoelectric effect by the reflecting plate are mixed and interact with photons, and produces and releases energy useful to living thing including the human body by adjusting the photoelectron energy while it is passing the color balancer and multiprism disks.

Therefore, the present invention has the advantage of activating living things by producing energy useful thereto and projecting it directly thereon applying the principle of producing energy in the cell of a living thing by means of an outside device.

It is understood that various other modifications will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art which this invention pertains.

What is claimed is:

1. A biological energy projector, comprising:
    an elongate housing;
    means for producing light energy provided in said housing at a first end thereof, said means for producing light energy comprising an electric light source;
    means for changing energy from one form to another provided at an intermediate portion of said housing, wherein said housing has a light reflecting interior surface, said light reflecting interior surface having a multiprism layer formed thereon, whereby said means for changing energy comprises said housing having said light reflecting interior surface and said multiprism layer formed on said light reflecting interior surface; and
    means for adjusting energy provided at an end of said housing opposite said means for producing light energy, said means for adjusting comprising:
        a color balancer having one side facing said means for producing light energy;
        a plurality of stacked prism disks provided on the opposite side of said color balancer from said means for producing light energy; and
        a plate member provided on the opposite side of said plurality of stacked prism disks from said color balancer and being constructed and arranged to pass energy transmitted by said plurality of stacked prism disks based on the intensity of the energy.

2. The biological energy projector as claimed in claim 1, wherein said housing is a stainless steel tube.

3. The biological energy projector as claimed in claim 1, wherein said means for producing light energy comprises a socket adapted for connection with an electricity source, an electric light bulb in said socket, and a switch for controlling a supply of electricity to said electric light bulb.

4. The biological energy projector as claimed in claim 3, wherein said switch is mounted on said housing.

5. The biological energy projector as claimed in claim 3, wherein said electric light bulb is one of an incandescent white light bulb and a fluorescent white light bulb.

6. The biological energy projector as claimed in claim 1, wherein said multiprism layer is a light-transmitting layer having one side provided with a plurality of projections, each projection having prismatic optical characteristics.

7. The biological energy projector as claimed in claim 1, wherein said color balancer is constructed and arranged to adjust energy passing therethrough to obtain a component of the energy passing therethrough.

8. The biological energy projector as claimed in claim 7, wherein said plurality of stacked prism disks is arranged to receive said component of energy obtained from said color balancer and is constructed and arranged to raise an intensity of said component of energy through spectral diffraction and interference as said component of energy passes through said plurality of stacked prism disks.

9. The biological energy projector as claimed in claim 7, wherein said color balancer is made from a blue acrylic material.

10. The biological energy projector as claimed in claim 9, wherein said color balancer is plate-shaped and about 1 mm to about 5 mm thick.

11. The biological energy projector as claimed in claim 1, wherein said housing is made from a metallic material having light-reflecting and photoelectric effect characteristics.

12. The biological energy projector as claimed in claim 1, wherein said plate member is a black body acrylic plate.

13. The biological energy projector as claimed in claim 1, wherein said means for producing light energy includes an electrical grounding device.

14. The biological energy projector as claimed in claim 13, wherein said electrical grounding device comprises a metal net at least partially surrounding said electric light source and a grounding wire connected to said metal net.

* * * * *